United States Patent

Schwab et al.

(10) Patent No.: US 6,500,975 B1
(45) Date of Patent: Dec. 31, 2002

(54) CATIONIC RUTHENIUM COMPLEXES, THEIR PRODUCTION AND THEIR USE

(75) Inventors: Peter Schwab, Bad Dürkheim (DE); Michael Schulz, Ludwigshafen (DE); Justin Wolf, Würzburg (DE); Wolfram Stuer, Würzburg (DE); Helmut Werner, Würzburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/674,536

(22) PCT Filed: May 3, 1999

(86) PCT No.: PCT/EP99/02992

§ 371 (c)(1),
(2), (4) Date: Nov. 2, 2000

(87) PCT Pub. No.: WO99/58538

PCT Pub. Date: Nov. 18, 1999

(30) Foreign Application Priority Data

May 8, 1998 (DE) .......................... 198 20 652

(51) Int. Cl.[7] .............................. C07F 15/00; B01J 31/00
(52) U.S. Cl. .................................. 556/22; 556/7; 556/8; 556/23; 556/30; 556/136; 556/137; 502/154; 502/155
(58) Field of Search ............................... 556/22, 23, 7, 556/8, 30, 136, 137; 502/154, 155

(56) References Cited

U.S. PATENT DOCUMENTS 5,621,047 A    4/1997   Nubel et al. ................. 525/247

FOREIGN PATENT DOCUMENTS

| EP | 218 138 | 4/1987 |
|---|---|---|
| WO | WO 93/20111 | 10/1993 |
| WO | WO 96/04289 | 2/1996 |
| WO | WO 97/06185 | 2/1997 |

OTHER PUBLICATIONS

Grünwald et al. "five–Coordinate 10–Electon Carbene– and Vinylideneruthenium (II) COmplexes prepared from $[RuCl_2(C_8H_{12})]_n$ or from the New Dihydridoruthenium (IV) Compound $[RuH_2Cl_2(P^iPr_3)_2]$" Organometallics (1996) vol. 15 pgs 1960–1962.

Oliván et al. "The first double oxidative addition of $CH_2Cl_2$ to a metal complex: facile synthesis of $[Ru(CH_2)Cl_2\{P(C_6H_{11})_3\}_2]$" J. Chem Soc. Commun. (1997) pp. 1733–1734.

Crowe et al. "Acrylonitriles Cross–Methathesis: Coaxing Olefin Metathesis Reactivity from a Reluctant Substrate" J. Am. Chem. Soc. vol. 117 (1995) pp. 5162–5163.

Stüer et al. "Carbynehydriodoruthenium Complexes as Catalysts for the Selective, Ring–Opening Methathesis of cyclopentene with Methyl Acrylate" Agnew. Chem. Int. Ed. vol. 37 (1998) pp. 3421–3423.

Primary Examiner—Porfirio Nazario-Gonzalez
(74) Attorney, Agent, or Firm—Keil & Weinkauf

(57) ABSTRACT

Cationic ruthenium complexes of the formula A or B or mixtures containing them,

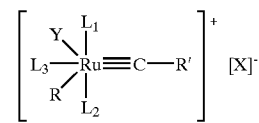

A

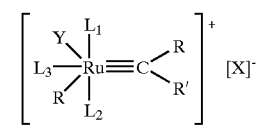

B where B may be stabilized by a further ligand $L_4$ and

X is an anion which does not coordinate or coordinates weakly to the metal center, Y is a monodentate or multidentate anionic ligand, R and R' are each, independently of one another, hydrogen or a substituted or unsubstituted $C_1$–$C_{20}$-alkyl, $C_6$–$C_{20}$-aryl or $C_7$–$C_{20}$-alkylaryl radical and $L_1$, $L_2$, $L_3$ and $L_4$ are, independently of one another, uncharged electron donor ligands, are described.

9 Claims, No Drawings

CATIONIC RUTHENIUM COMPLEXES, THEIR PRODUCTION AND THEIR USE

The present invention relates to cationic ruthenium complexes which can be used, for example, as catalysts in metathesis reaction and processes for their preparation.

Olefin metathesis (disproportionation) involves, in its simplest form, a reversible, metal-catalyzed transalkylidenation of olefins by rupture and reformation of carbon-carbon double bonds. In the case of the metathesis of acyclic olefins, a distinction is made, for example, between self-metathesis in which an olefin is transformed into a mixture of two olefins having different molar masses (for example conversion of propene into ethene and 2-butene) and cross-metathesis or cometathesis in which two different olefins react (for example propene with 1-butene to give ethene and 2-pentene). Further application areas of olefin metathesis include syntheses of unsaturated polymers by ring-opening metathesis polymerization (ROMP) of cyclic olefins and the acyclic diene metathesis polymerization (ADMET) of $\alpha,\omega$-dienes. More recent applications concern the selective ring opening of cyclic olefins by means of acyclic olefins, and also ring closure reactions (RCM) by means of which, preferably starting from $\alpha,\omega$-dienes, unsaturated rings of various ring sizes can be prepared.

Suitable catalysts for metathesis reactions are in principle homogeneous and heterogeneous transition metal compounds.

Heterogeneous catalysts, for example molybdenum, tungsten or rhenium oxides on inorganic oxidic supports, have high activity and regenerability in reactions of non-functionalized olefins but often have to be pretreated with an alkylating agent to increase the activity when using finctionalized olefins such as methyl oleate. Olefins having protic functional groups (such as hydroxyl groups, carboxyl groups or amino groups) lead to spontaneous deactivation of the heterogeneous catalyst.

In recent years, increased efforts have been made to prepare homogeneous catalysts which are stable in protic medium and in the presence of atmospheric oxygen. Here, specific ruthenium alkylidene compounds have attracted particular interest. Such complexes and processes for their preparation are known.

WO 93/20111 describes ruthenium- and osmium carbene complexes for olefin metathesis polymerization. The complexes have the structure $RuX_2(=CH-CH=CR_2)L_2$. Ligands L used are triphenylphosphine and substituted triphenylphosphine. The complexes are prepared, for example, by reacting $RuCl_2(PPh_3)_3$ with suitable disubstituted cyclopropenes as carbene precursors. However, the synthesis of cyclopropene derivatives involves a number of steps and is of little interest from a commercial point of view.

Similar reactions are described in WO 96/04289. Processes for olefin metathesis polymerization are also mentioned.

Use of such catalysts for peroxide crosslinking of ROMP polymers is described in WO 97/03096.

WO 97/06185 likewise describes metathesis catalysts which are based on ruthenium carbene complexes. Apart from the above-described method, they can also be prepared by reacting $RuCl_2(PPh_3)_3$ with diazoalkanes. However, handling diazoalkanes constitutes a safety risk, particularly when the process is carried out on an industrial scale.

In addition, the starting materials of the formula $RuCl_2(PPh_3)_3$ have to be prepared from $RuCl_3 3H_2O$ using a large excess of triphenylphosphine. In the catalyst synthesis itself, $PPh_3$ ligands are again lost as a result of ligand replacement. The carbene precursors used require multistage syntheses and do not keep indefinitely.

Organometallics 1996, 15, 1960 to 1962, describes a process for preparing ruthenium complexes in which polymeric $[RuCl_2(cyclooctadiene)]_x$ is reacted with hydrogen in i-propanol in the presence of phosphine. This eliminates the need for the phosphine replacement. An undefined mixture of products is obtained. In addition, long reaction times are necessary when starting from a polymeric starting material. The cyclooctadiene present in the starting material does not contribute to the reaction and is lost.

J. Chem. Soc. Commun. 1997, 1733 to 1734, describes a synthesis of the methylene complex $RuCl_2(=CH_2)(PCy_3)_2$, which starts from dichloromethane and the ruthenium polyhydride complex $RuH_2(H_2)_2(PCy_3)_2$. However, the ruthenium polyhydride complex is difficult to obtain. In addition, long reaction times are necessary.

The above ruthenium(II) alkylidene complexes, like all other known metathesis catalysts containing electron-rich transition metals, are unsuitable, or have only limited suitability, as catalysts for metathesis reactions of electron-poor olefins such as acrylic acid or derivatives thereof.

Catalyst systems based on molybdenum and tungsten have only very limited suitability for metathesis reactions of functionalized olefins. The most active catalysts involving electron-poor transition metals, e.g. the systems of the type $(RO)_2M(NR)(=CHR')(M=Mo, W)$ described in EP-A-0 218 138, suffer not only from the disadvantage of a low activity in respect of such substrates but also the disadvantage of an extremely high sensitivity to impurities in the feed and are also of no interest from an economic point of view because of their very high preparation costs. In J. Am. Chem. Soc. 1995, 117, 5162 to 5163, Crowe describes the use of these catalysts for mechanistic studies on cross-metathesis reactions of acrylonitrile ($H_2C=CHCN$) with $H_2C=CHR$ (R=electron-donating radical) to give $NCHC=CHR$ and $H_2C=CH_2$, which proceed to only moderate conversions even at high catalyst concentration. U.S. Pat. No. 5,621,047 describes the ring-opening cross-metathesis of cyclooctadiene with methyl methacrylate using $WCl_6/SnMe_4$ to give oligomers having carboxylic end groups.

Inexpensive catalyst systems which are stable to impurities in the feed and to atmospheric oxygen and are suitable for metathesis reactions in which electron-poor olefins participate are unknown hitherto.

It is an object of the present invention to develop a catalyst system for metathesis reactions of electron-poor olefins to enable metathesis reactions to be carried out on large-volume, basic industrial products such as acrylic acid and derivatives thereof, acrylonitrile, vinyl chloride, vinyl sulfone, etc. Apart from a high activity, a high stability to impurities in the feed and to atmospheric oxygen as well as a long operating life and inexpensive and uncomplicated synthesis from readily available raw materials should be realized.

We have found that this object is achieved by catalyst systems comprising as active components cationic ruthenium complexes of the formula A (cationic carbyne complexes) or B (cationic carbene complexes) or mixtures in which these are present,

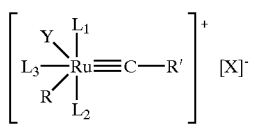

A

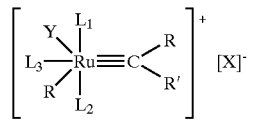

B where B may be stabilized by a further ligand $L_4$. In the structures A and B, —C $X^-$ is an anion which does not coordinate or coordinates only weakly to the metal center, for example a complex anion from main groups III to VII of the Periodic Table of the Elements, e.g. $BR''_4^-$ ($R''$=F or phenyl which may be substituted by one or more fluorine atoms or by polyfluorinated or perfluorinated $C_1$–$C_6$-alkyl radicals, for example $C_6H_{5-n}F_n$ where n=1 to 5), $PF_6^-$, $AsF_6^-$, $SbF_6^-$, $ClO_4^-$, $CF_3SO_3^-$ or $FSO_3^-$, Y is a monodentate or multidentate anionic ligand, R and R' are each, independently of one another, hydrogen or a substituted or unsubstituted $C_1$–$C_{20}$-alkyl, $C_6$–$C_{20}$-aryl or $C_7$–$C_{20}$-alkylaryl or aralkyl radical, $L_1$, $L_2$, $L_3$ and $L_4$ are, independently of one another, uncharged electron donor ligands, preferably nitrogen donors, for example amines and pyridines, phosphines, arsines, stibines, bearing at least two bulky radicals such as i-propyl, t-butyl, cyclopentyl, cyclohexyl, methyl or the like, or else π-coordinated olefins or solvent molecules.

The groups preferably have the following meanings:

$X^-$ is $BR''_4^-$ where $R''$=F or $C_6H_3$ (m-$CF_3$)$_2$,

Y is halogen, preferably chlorine, or OR where R=$C_1$–$C_6$-alkyl, $C_6$–$C_{12}$-aryl, preferably phenoxide, R is H, R' is $C_1$–$C_6$-alkyl, $C_6$–$C_{12}$-aryl, $C_7$–$C_{20}$-aralkyl, preferably methyl or benzyl, $L_1$, $L_2$ are phosphines bearing at least two bulky radicals, $L_3$, $L_4$ are cyclic or acyclic ethers or tertiary amines such as NMe$_2$phenyl, NMe$_3$, NEt$_3$.

The synthesis of the active components A and/or B or of mixtures in which these active components are present can be carried out starting from numerous organometallic starting materials, for example by reacting hydrido(vinylidene) complexes of the type RuY(H)(=C=CHR)$L_1L_2$, which can be synthesized by reacting RuClH(H$_2$)$L_1L_2$ with terminal alkynes HC≡CR, with $R^+X^-$, where $X^-$ is a non-coordinating or weakly coordinating anion. RuClH(H$_2$)$L_2$ can here be prepared as described in the literature, for example from the polymeric ruthenium precursor [RuCl$_2$(COD)]$_x$(COD=cyclooctadiene) in i-propanol in the presence of L under a hydrogen atmosphere (Werner et al., Organometallics 1996,15, 1960 to 1962) or starting from the same starting material in sec-butanol in the presence of L and tertiary amines (NEt$_3$) under a hydrogen atmosphere (Grubbs et al., Organometallics 1997, 16, 3867 to 3869). RuClH(H$_2$)$L_2$ is also obtainable starting from RuCl$_3$.H$_2$O in THF by reaction with L in the presence of activated magnesium under a hydrogen atmosphere (BASF AG, DE-A-198 00 934 which has earlier priority but is not a prior publication) and is preferably reacted in situ with 1-alkynes to give the corresponding hydrido(chloro)vinylidene complexes RuClH(=C=CHR)$L_2$. The latter can be isolated or react in situ with $H^+X^-$($X^-$=non-coordinating anion) to give the active components A and/or B of the present invention.

By reacting compounds of the type RuYY'(=CHR)$L_1L_2$ (where Y can be the same as Y') with $R^+X^-$, where $X^-$ is a non-coordinating or weakly coordinating anion. Mixed-anion alkylidene complexes RuXY(=CHCH$_2$R)$L_2$ can be prepared as described in DE-A-198 00 934 starting from RuXH(=C=CHR)$L_2$.

By reacting compounds of the type RuYY'(=CHR)$L_1L_2$ with anion-abstracting abstracting metal salts $M^+X^-$ or Lewis acids such as BF$_3$ of AlCl$_3$ in the presence of a ligand $L_3$, where $X^-$ is a non-coordinating or only weakly coordinating anion and the anionic ligands Y and Y' can be identical or different. MX can be, for example, AgPF$_4$, AgB(C$_5$F$_5$)$_4$, AgPF$_6$ or AgSbF$_6R^+X^-$, $M^+X^-$ and the corresponding Lewis acids are preferably used in a molar ratio, based on the organometallic starting material, of from 1:10 to 1000:1.

Reactions to give the active components A and/or B are preferably carried out in organic solvents under an inert gas atmosphere, preferably in solvents which can stabilize an unsaturated metal center by coordination, for example aliphatic or cyclic ethers such as dioxane or THF, amines, DMSO, nitriles, phosphines, arsines, stibines, water, olefins or other two-electron donors. The reaction is preferably carried out in THF at from −100 to +100° C., preferably from −80 to −40° C., and pressures of from 1 mbar to 100 bar, preferably from 0.5 to 5 bar.

The reaction can be carried out using one or more molar equivalents of $R^+X^-$. $L_{1-3}$RX formed when using excess $R^+X^-$does not adversely affect the reaction. The compositions comprising the active components A and/or B obtained in this way can be used in situ as a highly active metathesis catalyst system or can be stored at low temperatures under an inert gas atmosphere. If desired, the active components A or B are used in isolated form.

The reaction is generally complete after from 1 second to 10 hours, preferably after from 3 seconds to 1 hour. Suitable reaction vessels are glass or steel vessels in general, if desired lined with ceramic.

The components A and/or B or mixtures in which these components are present are highly active metathesis catalysts for linear and cyclic olefins.

The catalyst systems can be used, inter alia, for self-metathesis of an olefin or cross-metathesis or two or more olefins, ring-opening metathesis polymerization (ROMP) of cyclic olefins, selective ring opening of cyclic olefins using acyclic olefins, acyclic diene metathesis polymerization (ADMET), ring-closure metathesis (RCM)

and numerous metathesis variants.

In contrast to RuCl$_2$(=CHR)$L_2$, use of these catalyst systems enables for the first time electron-poor olefins of the type $R^aR^bC$=CR$^c$Z, where $R^a$, $R^b$, $R^c$ are, independently of one another, hydrogen, $C_1$–$C_{12}$-alkyl or $C_6$–$C_{12}$-aryl and Z is an electron-withdrawing radical such as CO$_2R^d$, CONH$_2$, COX, CN where X is halogen and $R^d$ is hydrogen, $C_1$–$C_{12}$-alkyl or $C_1$–$C_{12}$-aryl, to be reacted efficiently and with very high activity even under mild reaction conditions. Examples which may be mentioned are acrylic acid and its derivatives, fumaric and maleic esters, maleic anhydride, vinyl chloride, methyl vinyl ketone and others.

The invention is illustrated by the examples below.

EXAMPLES

Example 1

Preparation of $RuHCl(H_2)(PCy_3)_2$

A brown suspension of 300 mg (1.07 mmol) of $[RuCl_2(C_8H_{12})]_n$ and 982 mg (3.50 mmol) of tricyclohexylphosphine in 15 ml of 2-butanol is stirred under an $H_2$ atmosphere (1 bar) for 2.5 hours at 110° C.; an orange-red solution is formed and an orange-red solid is precipitated. After cooling to room temperature, the solid is filtered off, washed cold with 3×5 ml of acetone and dried under reduced pressure.

Yield: 559 mg (75%).

Example 2

Preparation of $RuHCl(=C=CH_2)(PCy_3)_2$

Acetylene is passed for about 30 seconds, while stirring, into a solution of 102 mg (0.15 mmol) of $RuHCl(H_2)(PCy_3)_2$ from Example 1 in $CH_2Cl_2$ cooled to −78° C. The solvent is removed under reduced pressure and the brown solid is washed with 5 ml of cold pentane and dried under reduced pressure.

Yield: 99 mg (94%).

Example 3

Reaction of $RuHCl(=C=CH_2)(PCy_3)_2$ with $[PhNMe_2H][B(C_6F_5)_4]$
Preparation of $[RuClH=CMe)(NMe_2Ph)-(PCy_3)_2][B(C_6F_5)_4]$ 1

72 mg (0.10 mmol) of $RuHCl(=C=CH_2)(PCy_3)_2$ from Example 2 are mixed, as solid, with 80 mg (0.10 mmol) of $[PhNMe_2H][B(C_6F_5)_4]$ and, after cooling to −80° C., admixed with 10 ml of $CH_2Cl_2$. The reaction mixture spontaneously becomes yellow. The complex 1 formed was identified unambiguously by spectroscopy (figures in ppm). According to NMR, the reaction proceeds quantitatively.

$^1$H-NMR (200 MHz, $CD_2Cl_2$, −60° C.): δ=7.32 −6.97 (m, 5H, Ph—H), 3.0–1.2 (m, 75 H, $PCy_3$ and Me—H), −6.33 (+, $^2J_{PH}$=14.5 Hz, 1H, RuH); $^{19}$F-NMR (376.4 MHz, $CD_2Cl_2$, −70° C.): δ=133.3 (s), −162.5 (s), −166.4 (s); $^{31}$P-NMR (162.0 MHz, $CD_2Cl_2$, −70° C.): δ=56.6 (s, $PCy_3$); $^{13}$C-NMR (100.6 MHz, $CD_2Cl_2$, −70° C.): δ=311.9 (s broad, Ru≡C—Me), 148.6, 146.2, 138.9, 137.0, 134.5 and 129.1 (each s, Ph—C or $C_{ipso}$ of $C_6F_5$), 136.4 (t, $C_{ipso}$ of $C_6F_5$ or PH—C), 123.2, 118.1 and 113.4 (each m, $C_6F_5$), 41.5 (s broad, NMe), 40.2 (s, Ru≡C—Me), 34.0 (vt, N=22.5 Hz, $C_a$ of $PCy_3$), 30.6, 28.9, 26.7, 26.4 and 25.3 (each s, $PCy_3$).

Example 4

Reaction of $RuHCl(=C=CH_2)(PCy_3)_2$ with $HBF_4$ in $Et_2O$ Preparation of $[RuClH(=C—Me)(OEt_2)—(PCy_3)_2][BF_4]$ 2

102 mg (0.14 mmol) of $RuHCl(=C=CH_2)(PCy_3)_2$ from Example 2 are dissolved in a mixture of 5 ml of $CH_2Cl_2$ and 5 ml of $Et_2O$. The reddish brown solution is admixed at −80° C. with an excess of a solution of $HBF_4$ in $Et_2O$ (about 0.1 ml of a 1.6 M solution of $HBF_4$ in $Et_2O$). The brown solution is warmed to about 0° C. and the solvent is removed under reduced pressure. The brown residue is admixed with 5 ml of $Et_2O$ and stirred for a few minutes, forming a yellow solid. The supernatant brown solution is discarded and the yellow solid 2 is washed once more with 5 ml of $Et_2O$.

Yield: 90 mg (72%).

Conductivity ($CH_2Cl_2$, 20° C.): $\Delta$=47 cm$^2$ $\Omega^{-1}$mol$^{-1}$ $^1$H-NMR (400.1 MHz, $CD_2Cl_2$, 28° C.): δ=4.77 (q, $J_{PH}$=7.2 Hz, 4 H, $OCH_2CH_3$), 2.52 –1.30 (m, 75 H, $CH_3$, $PCy_3$), −6.91 (t, $J_{PH}$=15.0 Hz, 1H, Ru—H); $^{19}$F-NMR (188 MHz, $CD_2Cl_2$, 28° C.): δ=−152.6 (s); $^{31}$P-NMR (162.0 MHz, $CD_2Cl_2$, 28° C.): δ=55.5 (s, $PCy_3$); $^{13}$C-NMR (100.6 MHz, $CD_2Cl_2$, 28° C.): δ=84.6 (s, $OCH$hd 2$CH_3$), 41.4 (s, Ru≡C—Me), 35.7 (vt, N=22.1 Hz, $C_a$ of $PCy_3$), 31.2 and 30.4 (each S, $PCy_3$), 27.6 and 27.3 each vt, N=10.2 Hz, $PCy_3$), 26.2 (s, $PCy_3$), 12.7 (s, $OCH_2CH_3$ ); the carbyne C atom was not detected.

Reaction of 2 with $H_2O$ results in ligand replacement to give $[RuClH(≡C—Me)(OH_2)(PCy_3)_2]$ $[BF_4]$: $^1$H-NMR (400.1 MHz, $CD_2Cl_2$, 60° C.): δ2.49–2.37, 1.94–1.09 (each m, 71 H, $CH_3$, $H_2O$, $PCy_3$) −6.48 (t broad, 1H, Ru—H); $^{19}$F-NMR (376.4 MHz, $CD_2Cl_2$, −60° C.): δ=151.4 (s); $^{31}$P-NMR (162.0 MHz, $CD_2Cl_2$, −60° C.): δ=56.2 (s, $PCy_3$); $^{13}$C-NMR (100.6 MHz, $CD_2Cl_2$, −60° C.): δ=313.9 (m broad, Ru≡C—Me), 40.8 (s, Ru≡C—Me), 34.1 (vt, N=22.0 Hz, $C_a$ of $PCy_3$), 30.6, 29.0, 26.8, 26.5 and 25.4 (each s, $PCy_3$).

Example 5

Progressive Reaction of $RuHCl(=C=CH_2)(PCy_3)_2$ with $CF_3SO_3H$ and $HBF_4$ 6.8 μl (0.08 mmol) of $CF_3SO_3H$ are added dropwise at −78° C. to the brown solution of 56 mg (0.08 mmol) of $RuHCl(=C=CH_2)(PCy_3)_2$ from Example 2 in 2 ml of THF. After stirring for 10 minutes at −78° C., 2 ml of a 1.6 M solution of $HBF_4$ in ether (3.20 mmol) are added. This gives a yellowish brown solution 3.

Example 6

Ring-opening Metathesis Polymerization (ROMP) of Cyclooctene Using Mixture 3

4 ml (30.7 mmol) of cyclooctene are treated at room temperature with a few drops of the mixture 3. After 2 minutes, the solution is highly viscous. After appropriate work-up, 3.5 g (99%) of polyoctene are isolated. Comparable results are obtained using the catalysts 1 and 2.

Example 7

Selective Ring-opening Metathesis (ROM) of Cyclopentene with Methyl Acrylate

A mixture of 50 ml (0.56 mol) of methyl acrylate and 4 ml (0.05 mmol) of cyclopentene is treated at room temperature with a few drops of the mixture 3 and then stirred for 2 hours. Subsequently, excess substrate and solvent are distilled off at atmospheric pressure, the residue which remains is admixed with 10 ml of pentane and, to remove metal residues, filtered through aluminum oxide (neutral, activity grade III, height of bed =2 cm) with addition of 60 ml of $Et_2O$ as solvent. Distilling off the solvent leaves 2.5 g of a colorless liquid. This comprises the first members of the homologous series of long-chain and polyunsaturated esters $C_7H_{11}CO_2Me$, $C_{12}H_{19}CO_2Me$ and $C_{17}H_{27}CO_2Me$ in selectivities of 50, 40 and 10%. Comparable results are obtained using catalysts 1 and 2.

We claim:

1. A cationic ruthenium complex of the formula A or B or a mixture in which it is present

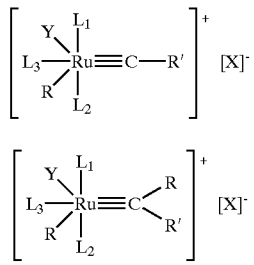

where B may be stabilized by a further ligand $L_4$ and
X is an anion which does not coordinate or coordinates only weakly to the metal center,
Y is a monodentate or multidentate anionic ligand,
R and R' are each, independently of one another, hydrogen or a substituted or unsubstituted $C_1$–$C_{20}$-alkyl, $C_6$–$C_{20}$-aryl or $C_7$–$C_{20}$-alkylaryl radical and
$L_1$, $L_2$, $L_3$ and $L_4$ are, independently of one another, uncharged electron donor ligands.

2. A ruthenium complex as claimed in claim 1, wherein the uncharged electron donor ligands are phosphines, arsines, stibines each bearing at least two bulky radicals, amines, pyridines, π-coordinated olefins or solvent molecules.

3. A process for preparing cationic ruthenium complexes as claimed in claim 1 by reacting an uncharged vinylidene complex of the formula $RuY(H)(=C=CHR)L_1L_2$ with $R^+X^-$, where $X^-$ is an anion or complex anion which does not coordinate or coordinates only weakly to the metal center and $R^+$ is $H^+$, $alkyl^+$, $aryl^+$, $alkylaryl^+$ or a complex cation of the type $LH^+$.

4. A process for preparing cationic ruthenium complexes as claimed in claim 1 by reacting uncharged alkylidene complexes of the type $RuYY'(=CHR)L_1L_2$, where Y can be the same as Y', with $R^+X^-$; where $X^-$ is an anion or complex anion which does not coordinate or coordinates weakly to the metal center and $R^+$ is $H^+$, $alkyl^+$, $aryl^+$, $alkylaryl^+$ or a complex cation of the type $LH^+$.

5. A process for preparing cationic ruthenium complexes as claimed in claim 1 by reacting compounds of the type $RuYY'(=CHR)L_1L_2$ with anion-abstracting metal salts $M^+X^-$ or Lewis acids in the presence of a ligand $L_3$, where $X^-$ is a non-coordinating or weakly coordinating anion and the anionic ligands Y and Y' can be identical or different.

6. A process as claimed in claim 3, wherein $R^+X^-$ is an acid compound $H^+X^-$ or $LH^+X^-$, where $X^-$ is a non-coordinating or weakly coordinating anion or complex anion and L is a two-electron donor ligand.

7. A process as claimed in claim 6, wherein $R^+X^-$ is $CF_3SO_3H$, $F_3CCO_2H$, $HClO_4$, $HBF_4$, $HPF_6$, $HSbF_6$ or $[PhNMe_2H][B(C_6F_5)_4]$.

8. A process as claimed in claim 5, wherein the anion-abstracting metal salts $M^+X^-$ used are salts in which $M^+$ forms a sparingly soluble, new metal salt with the anions to be abstracted and $X^-$ is a non-coordinating or weakly coordinating anion.

9. A process as claimed in claim 8, wherein $M^+X^-$ is $AgBF_4$, $AgB(C_5F_5)_4$, $AgPF_6$ or $AgSbF_6$.

* * * * *

UNITED STATES PATENT AND TRADEMARK OFFICE
CERTIFICATE OF CORRECTION

PATENT NO.    : 6,500,975 B1
DATED         : December 31, 2002
INVENTOR(S)   : Schwab et al.

It is certified that error appears in the above-identified patent and that said Letters Patent is hereby corrected as shown below:

<u>Title page,</u>
Item [57], in formula B in the ABSTRACT and Column 7, lines 13-17, the triple bond between "Ru" and "C" should be a double bond.

Signed and Sealed this

Twentieth Day of May, 2003

JAMES E. ROGAN
*Director of the United States Patent and Trademark Office*